US012687512B2

(12) United States Patent
Choi et al.

(10) Patent No.: US 12,687,512 B2
(45) Date of Patent: Jul. 21, 2026

(54) IMPEDANCE SPECTROSCOPY ANALYTICAL METHOD FOR CONCRETE USING MACHINE LEARNING, RECORDING MEDIUM AND DEVICE FOR PERFORMING THE METHOD

(71) Applicant: Foundation of Soongsil University—Industry Cooperation, Seoul (KR)

(72) Inventors: Hajin Choi, Seoul (KR); Joo-hye Park, Seoul (KR); Do-yun Kim, Seoul (KR); So-hyun Sim, Seoul (KR); Jin-Young Hong, Seoul (KR)

(73) Assignee: FOUNDATION OF SOONGSIL UNIVERSITY-INDUSTRY COOPERATION, Seoul (KR)

( * ) Notice: Subject to any disclaimer, the term of this patent is extended or adjusted under 35 U.S.C. 154(b) by 362 days.

(21) Appl. No.: 18/033,742

(22) PCT Filed: Nov. 17, 2021

(86) PCT No.: PCT/KR2021/016839
§ 371 (c)(1),
(2) Date: Apr. 25, 2023

(87) PCT Pub. No.: WO2022/139184
PCT Pub. Date: Jun. 30, 2022

(65) Prior Publication Data
US 2023/0400427 A1     Dec. 14, 2023

(30) Foreign Application Priority Data
Dec. 24, 2020     (KR) ........................ 10-2020-0182823

(51) Int. Cl.
*G01N 27/02*          (2006.01)
*G01N 33/38*          (2006.01)

(52) U.S. Cl.
CPC ......... *G01N 27/026* (2013.01); *G01N 33/383* (2013.01)

(58) Field of Classification Search
CPC .. G01N 27/026; G01N 27/041; G01N 27/221; G01N 27/223; G01N 33/383; G01N 29/09; G06N 20/00
See application file for complete search history.

(56) References Cited

U.S. PATENT DOCUMENTS

| | | | | |
|---|---|---|---|---|
| 9,625,403 | B1 * | 4/2017 | Hussain ................. | G01N 17/02 |
| 2004/0064265 | A1 | 4/2004 | Myers et al. ................... | 702/32 |
| 2018/0209951 | A1 * | 7/2018 | Vipulanandan ...... | G01N 33/383 |

FOREIGN PATENT DOCUMENTS

| | | |
|---|---|---|
| CN | 106290485 A | 1/2017 |
| CN | 109143108 A | 1/2019 |

(Continued)

OTHER PUBLICATIONS

Guangling Song, Cement and Concrete Research 30 (2000) 1723-1730, Equivalent circuit model for AC electrochemical impedance spectroscopy of concrete.

(Continued)

*Primary Examiner* — Manuel L Barbee
(74) *Attorney, Agent, or Firm* — Stein IP, LLC

(57) ABSTRACT

Provided is an impedance spectroscopy analytical method for concrete using machine learning. The method comprises identifying electrical flow through moisture and a conductive ion present in concrete using a node that measures electricity based on electrochemical impedance spectroscopy (EIS); generating a theoretical equivalent circuit model comprising a conductive path reflecting the electrical flow; normalizing an equivalent circuit reflecting a concrete microstructure based on an impedance experiment using the theoretical equivalent circuit model; and generating a predictive model for estimating a water and cement ratio from (Continued)

START

IDENTIFY ELECTRICAL FLOW INSIDE CONCRETE USING EIS — S10

GENERATE THEORETICAL EQUIVALENT CIRCUIT MODEL COMPRISING CONDUCTIVE PATH — S20

NORMALIZE EQUIVALENT CIRCUIT BASED ON IMPEDANCE EXPERIMENT — S30

GENERATE PREDICTIVE MODEL FOR ESTIMATING WATER AND CEMENT RATIO — S40

END a parameter value of the equivalent circuit through machine learning. Accordingly, the accuracy and reliability of estimating the microstructure and mixing ratio of the cement-based material can be increased.

9 Claims, 9 Drawing Sheets

(56)                      References Cited

FOREIGN PATENT DOCUMENTS

| JP | 2003-520974 | A | 7/2003 |
|----|-------------|----|---------|
| JP | 2020-115146 | A | 7/2020 |
| JP | 6794039 | B2 | 12/2020 |
| KR | 10-1221684 | B1 | 1/2013 |
| WO | WO 2019/125472 | A2 | 6/2019 |

OTHER PUBLICATIONS

W.J. McCarter, Cement and Concrete Research, vol. 24, No. 6, pp. 1097-1110, 1994, A Parametric Study of the Impedance Characteristics of Cement-Aggregate Systems During Early Hydration.

Lee, Jun-Cheol et al. Setting Characteristic Assessment of Cementitious Materials using Electrical Impedance Spectroscopy, Journal of the Korean Recycled Construction Resources Institute, Oct. 2017, vol. 5, No. 4, pp. 474-480.

Joohye Park et al., Water-Cement Ratio Estimation of Cementitious Materials Using Electrochemical Impedance Spectroscopy and Machine Learning, Journal of the Korea Concrete Institute, vol. 33, No. 4, pp. 353-361, Aug. 2021.

Chinese Office Action dated Aug. 9, 2025, issued to Chinese Application No. 202180069922.6.

"Research on Fresh Concrete Water-cement Ratio Based on Resistivity Method", Haibo Ren et al., Applied Mechanics and Materials, vol. 847, pp. 469-475.

* cited by examiner

IMPEDANCE SPECTROSCOPY ANALYTICAL METHOD FOR CONCRETE USING MACHINE LEARNING, RECORDING MEDIUM AND DEVICE FOR PERFORMING THE METHOD

TECHNICAL FIELD

The present invention relates to an impedance spectroscopy analytical method for concrete using machine learning, and to a recording medium and apparatus for performing the same, and more particularly, it relates to a technique of theoretically normalizing an equivalent circuit and applying machine learning to the result to improve the analytical problems of impedance spectroscopy method applied to cement-based materials.

BACKGROUND ART

Quality control at construction sites is a very important factor in guaranteeing the performance and durability of structures and for the safety of users. Accordingly, the Construction Technology Promotion Act stipulates detailed standards for quality control and procedures at domestic construction sites in the "Construction Quality Control Guidelines." In addition, the need to introduce technologies related to the 4th industrial revolution that can be applied to construction sites according to smart construction policies is emerging.

However, quality control technologies that can be applied in practice at fast-paced construction sites are very limited. In particular, the quality test for unhardened concrete (including ready-mixed concrete), which is the most used material, is limited to basic items such as slump, air volume, and chloride content. Among them, the slump test is a criterion for determining the workability of materials and is not suitable for quality control of the performance and durability of structures.

In addition, in the case of the air volume test method that has been used for a long time, the test method is a passive technique that can vary depending on the skill of field technicians. It is necessary to develop a simple and automated field test method while measuring and predicting the long-term and short-term performance of structures, which is the purpose of quality control.

Electrochemical Impedance Spectroscopy (EIS) is a nondestructive technique that uses a node that measures electricity to identify the electrical flow with moisture and conductive ions present inside a target material. Specifically, after applying a minute alternating current to the target material, the internal constituent material may be estimated by deriving impedance on the premise of an electrical equivalent circuit reflecting the microstructure.

Impedance spectroscopy based on electrochemistry has the advantage of being very simple to use and is being applied to various fields. In particular, in Korea, it is being used as a method of analyzing the body composition of the human body under the name of "InBody."

Various studies using impedance spectroscopy have also been conducted on cement-based materials represented by concrete. Research has been conducted mainly to predict early corrosion of reinforcing bars inside concrete. In the case of research on pure cement-based materials, studies on compressive strength estimation and condensation time measurement were conducted based on the impedance change according to the mixing ratio.

Despite various studies, the development of test methods for estimating internal components of cement-based materials using impedance spectroscopy is very limited. The reasons for this are 1) insufficient research on the equivalent circuit for deriving impedance, and 2) insufficient research on the correlation between resistance and capacitance constituting impedance and the internal constituents of cement-based materials.

In the case of the equivalent circuit of impedance spectroscopy applied to concrete, there are a total of 10 different circuit theories based on the consequential analysis of each study. The resulting resistance and capacitance are very different depending on the application of each circuit, so the general interpretation of the results is limited. In addition, since the number of resistances and capacitances is also different depending on the applied circuit, it is not easy to derive a correlation with constituent materials such as a mixing ratio.

PRIOR ART

Patent Literature

JP 2020-115146 A
JP 2003-520974 A
KR 10-1221684 B1

Non-Patent Literature

Shin, S. W., Hwang, G., & Lee, C. J. (2014), Electrical impedance response model of concrete in setting process, Journal of the Korean Society of Safety, 29 (5), 116-122.

DISCLOSURE

Technical Problem

Accordingly, the technical problem of the present invention is focused on this point, and an object of the present invention is to provide an impedance spectroscopy analytical method for concrete using machine learning.

Another object of the present invention is to provide a recording medium, on which a computer program for performing the impedance spectroscopy analytical method for concrete using machine learning is recorded.

Another object of the present invention is to provide an apparatus for performing the impedance spectroscopy analytical method for concrete using machine learning.

Technical Solution

In order to achieve the above object of the present invention, an impedance spectroscopy analytical method for concrete using machine learning according to an embodiment of the present invention comprises identifying electrical flow through moisture and a conductive ion present in concrete using a node that measures electricity based on Electrochemical Impedance Spectroscopy (EIS); generating a theoretical equivalent circuit model comprising a conductive path reflecting the electrical flow; normalizing an equivalent circuit reflecting a concrete microstructure based on an impedance experiment using the theoretical equivalent circuit model; and generating a predictive model for estimating a water and cement ratio from a parameter value of the equivalent circuit through machine learning.

In an embodiment of the present invention, the concrete microstructure includes a cement matrix and an internal void.

In an embodiment of the present invention, the machine learning uses at least one model of square exponential function Gaussian Process Regression (GPR), Support Vector Regression (SVR), and Decision Tree.

In an embodiment of the present invention, the parameter value includes resistance and capacitance of the equivalent circuit.

In an embodiment of the present invention, identifying the electrical flow applies a three-electrode method using a working electrode (WE), a counter electrode (CE), and a reference electrode.

In order to achieve the other object of the present invention, a computer program for performing the impedance spectroscopy analytical method for concrete using machine learning is recorded in a computer-readable storage medium.

In order to achieve another object of the present invention, an impedance spectroscopy analytical apparatus for concrete using machine learning according to an embodiment of the present invention comprises an Electrochemical Impedance Spectroscopy (EIS) unit for identifying electrical flow through moisture and a conductive ion present in concrete using a node that measures electricity based on EIS; an equivalent circuit unit for generating a theoretical equivalent circuit model comprising a conductive path reflecting the electrical flow; a circuit normalization unit for normalizing an equivalent circuit reflecting a concrete microstructure based on an impedance experiment using the theoretical equivalent circuit model; and a predictive model unit for generating a predictive model for estimating a water and cement ratio from a parameter value of the equivalent circuit through machine learning.

In an embodiment of the present invention, the concrete microstructure includes a cement matrix and an internal void.

In an embodiment of the present invention, the machine learning uses at least one model of square exponential function Gaussian Process Regression (GPR), Support Vector Regression (SVR), and Decision Tree.

In an embodiment of the present invention, the parameter value includes resistance and capacitance of the equivalent circuit.

In an embodiment of the present invention, the EIS unit applies a three-electrode method using a working electrode (WE), a counter electrode (CE), and a reference electrode.

Advantageous Effects

According to the impedance spectroscopy analytical method for concrete using machine learning, electrodes are installed on unhardened cement-based materials to immediately respond to changing conditions in the field through electrical measurement, and accordingly, mixture information such as water-cement ratio, etc. can be derived. Therefore, through the present invention, inverse estimation of the material mixture and durability prediction is possible, and it can be used as basic data for developing highly reliable quality control techniques for unhardened concrete at construction sites.

In addition, the present invention can contribute to the development of a simple, automated and highly reliable field test method by systematizing the quality control work performed based on existing manpower based on machine learning.

4

DESCRIPTION OF DRAWINGS

These and/or other aspects will become apparent and more readily appreciated from the following description of the embodiments, taken in conjunction with the accompanying drawings in which:

FIG. 6 is a graph of water-cement ratio prediction results according to the machine learning model using the square exponential function GPR of the present invention;

FIG. 7 is a graph of water-cement ratio prediction results according to the machine learning model using the SVR of the present invention;

FIG. 8 is a graph of water-cement ratio prediction results according to the machine learning model using the decision tree of the present invention.

DETAILED DESCRIPTION OF EMBODIMENTS

Figure 1:
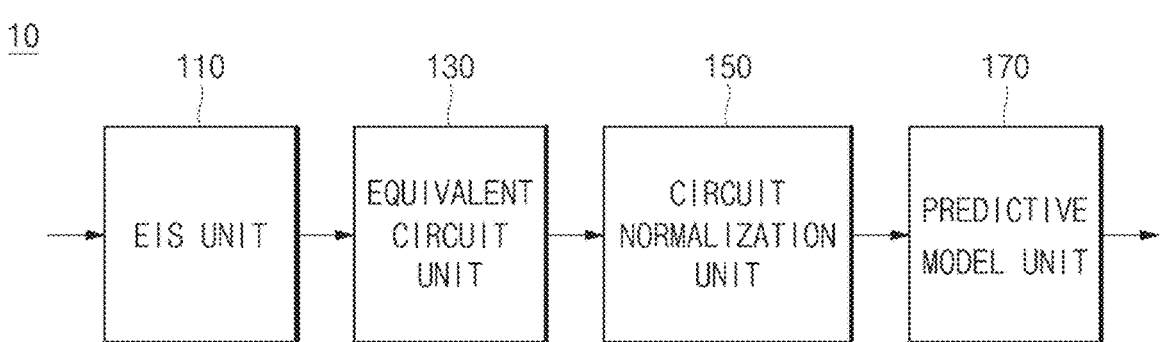
FIG. 1 is a block diagram of an impedance spectroscopy analytical apparatus for concrete using machine learning according to an embodiment of the present invention.

The detailed description of the present invention refers to the accompanying drawings which illustrate, by way of illustration, specific embodiments in which the present invention may be practiced. These embodiments are described in sufficient detail to enable those skilled in the art to practice the present invention. It should be understood that the various embodiments of the present invention are different from each other but are not necessarily mutually exclusive. For example, specific shapes, structures, and characteristics described herein may be implemented in another embodiment without departing from the spirit and scope of the invention in connection with one embodiment. Additionally, it should be understood that the position or arrangement of individual components within each disclosed embodiment may be changed without departing from the spirit and scope of the invention. Accordingly, the detailed description set forth below is not to be taken in a limiting sense, and the scope of the present invention, if properly described, is limited only by the appended claims, along with all equivalents as claimed by those claims. Like reference numbers in the drawings indicate the same or similar function throughout the various aspects.

Hereinafter, preferred embodiments of the present invention will be described in more detail regarding the drawings.

FIG. 1 is a block diagram of an impedance spectroscopy analytical apparatus for concrete using machine learning according to an embodiment of the present invention.

In order to improve the analytical problems of impedance spectroscopy applied to cement-based materials, an impedance spectroscopy analytical apparatus for concrete using machine learning (10, hereinafter apparatus) according to the present invention theoretically normalizes the equivalent circuit and applies machine learning to the result. Applying a theoretical model considering the microstructure of cement-based materials can normalize the circuit parameters (resistance, capacitance) and derive the impact on the mixing ratio more objectively.

In addition, machine learning can derive correlations from a new perspective by overcoming the limitations of existing regression analysis. To this end, the normalization and database of the equivalent circuit model were established through a literature review of the existing impedance spectroscopy method, and the results were verified experimentally. Specifically, by estimating the water-cement ratio (w/c ratio) of cement paste, which is the basic step of cement-based materials, it can be used for material mixture inverse estimation and durability prediction. In addition, it can be used as basic data for developing reliable quality control techniques for unhardened concrete at construction sites in the future.

Referring to FIG. 1, the apparatus 10 according to the present invention includes an EIS unit 110, an equivalent circuit unit 130, a circuit normalization unit 150, and a predictive model unit 170.

In the apparatus 10 of the present invention, software (application) for analyzing the impedance spectroscopy for concrete using machine learning may be installed and executed, and the configurations of the EIS unit 110, the equivalent circuit unit 130, the circuit normalization unit 150 and the predictive model unit 170 may be controlled by the software for analyzing the impedance spectroscopy for concrete using the machine learning executed in the apparatus 10.

The apparatus 10 may be a separate terminal or a part of a module of the terminal. In addition, the configuration of the EIS unit 110, the equivalent circuit unit 130, the circuit normalization unit 150, and the predictive model unit 170 may be formed as an integrated module or composed of one or more modules. However, on the contrary, each component may be composed of a separate module.

The apparatus 10 may be mobile or stationary. The apparatus 10 may be in the form of a server or engine, and can be called by other terms such as a device, a terminal, a user equipment (UE), a mobile station (MS), a wireless device or handheld device, etc.

The apparatus 10 may execute or manufacture various software based on an operating system (OS), that is, a system. The operating system is a system program for enabling software to use the hardware of the apparatus, and can include all mobile computer operating systems such as Android OS, iOS, Windows mobile OS, Bada OS, Symbian OS and Blackberry OS, and computer operating systems such as Windows-based, Linux-based, Unix-based, MAC, AIX, and HP-UX.

The EIS unit 110 identifies the electrical flow through moisture and conductive ions present in the concrete using a node that measures electricity based on electrochemical impedance spectroscopy (EIS).

In the case of impedance spectroscopy applied to cement-based materials, various equivalent circuits have been proposed according to the purpose of each study. Specifically, the circuit model that identifies the microstructure of cement-based materials based on electrical properties comprises a brick model considering the interfacial reaction between solid and liquid, a circuit including all conductive paths, a non-contact circuit model, and a circuit model of a continuous/discontinuous conductive path, etc.

Circuits based on the simulation approach include a circuit model including a capacitive element having a phase angle and a circuit model fitting the impedance spectrum of cement paste. Various equivalent circuits that respond to electrical changes that change when pozzolan, insulating particles, and fibers are introduced have also been proposed. In addition, a circuit modeling the chloride transport phenomenon for the purpose of reinforcing steel corrosion was also proposed. Circuits that fit the impedance spectrum of hardened and unhardened concrete also exist.

Figure 2:
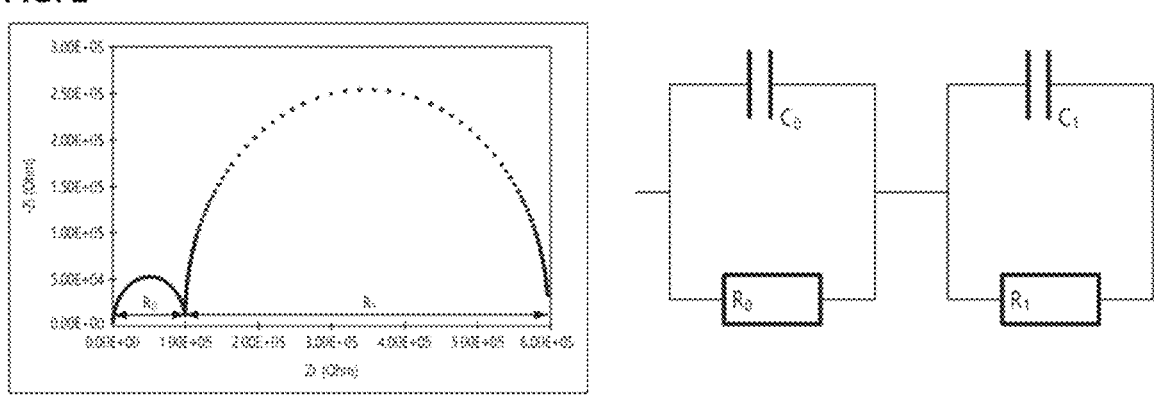
FIG. 2 is a diagram for describing the normalization of an experimental equivalent circuit of the present invention into a theoretical equivalent circuit, in which the microstructure of concrete is reflected.
Figure 2:
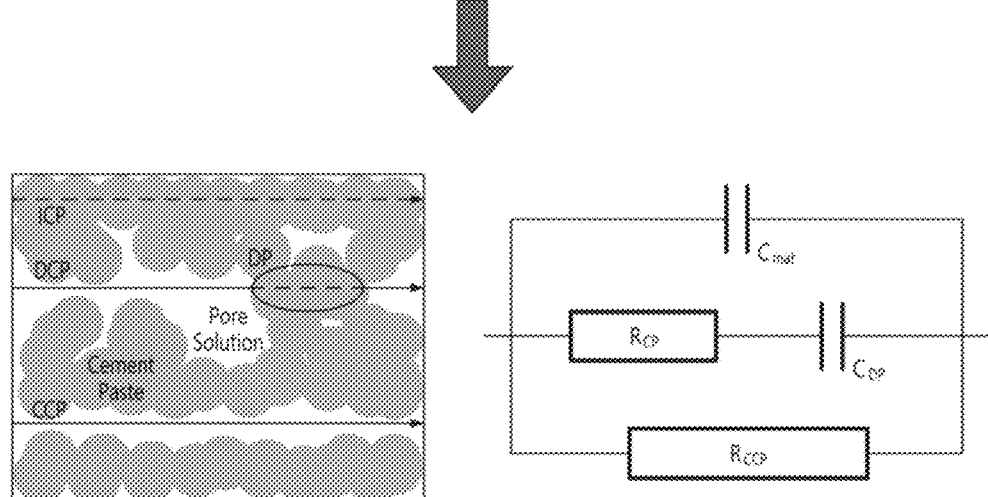

In one embodiment of the present invention, a model that reflects the microstructure of cement-based materials and is used for unhardened concrete is shown in FIG. 2. This is a circuit, in which circuits, in which one resistance and one capacitance are connected in parallel and are continuously arranged, and when viewed from the Nyquist plot, two arcs appear side by side and one arc corresponds to one parallel circuit.

Referring to FIG. 2, the arc seen in the first half of the Nyquist plot corresponds to a high-frequency section as a bulk arc, and represents the size of the electrolyte impedance between the working electrode and the reference electrode. The arc that follows is the electrode arc, which is the result of a reaction between the electrode and the concrete contact surface. The circuit, in which $R_1$ and $C_1$ are connected in parallel, is involved in the bulk reaction, and the circuit, in which $R_2$ and $C_2$ are connected in parallel, is involved in the electrode reaction, and this circuit has been mainly used in research on unhardened cement-based materials.

The equivalent circuit unit 130 generates a theoretical equivalent circuit model comprising a conductive path reflecting the electrical flow.

An example, in which a theoretical equivalent circuit is assumed based on the microstructure of a cement-based material, is shown in FIG. 2. Depending on the continuity inside the composite material when current flows, a model, in which the different circuits are connected in parallel, can be replaced. For example, the microstructure can be defined in terms of the flow of current with ICP (Insulator Conductive Path) that passes only cement paste, CCP (Continuous Conductive Path) that passes through the path connected with micropores, and DCP (Discontinuous Conductive Path) that passes through DP (Discontinuous Point) while passing through micropores.

Figure 3:
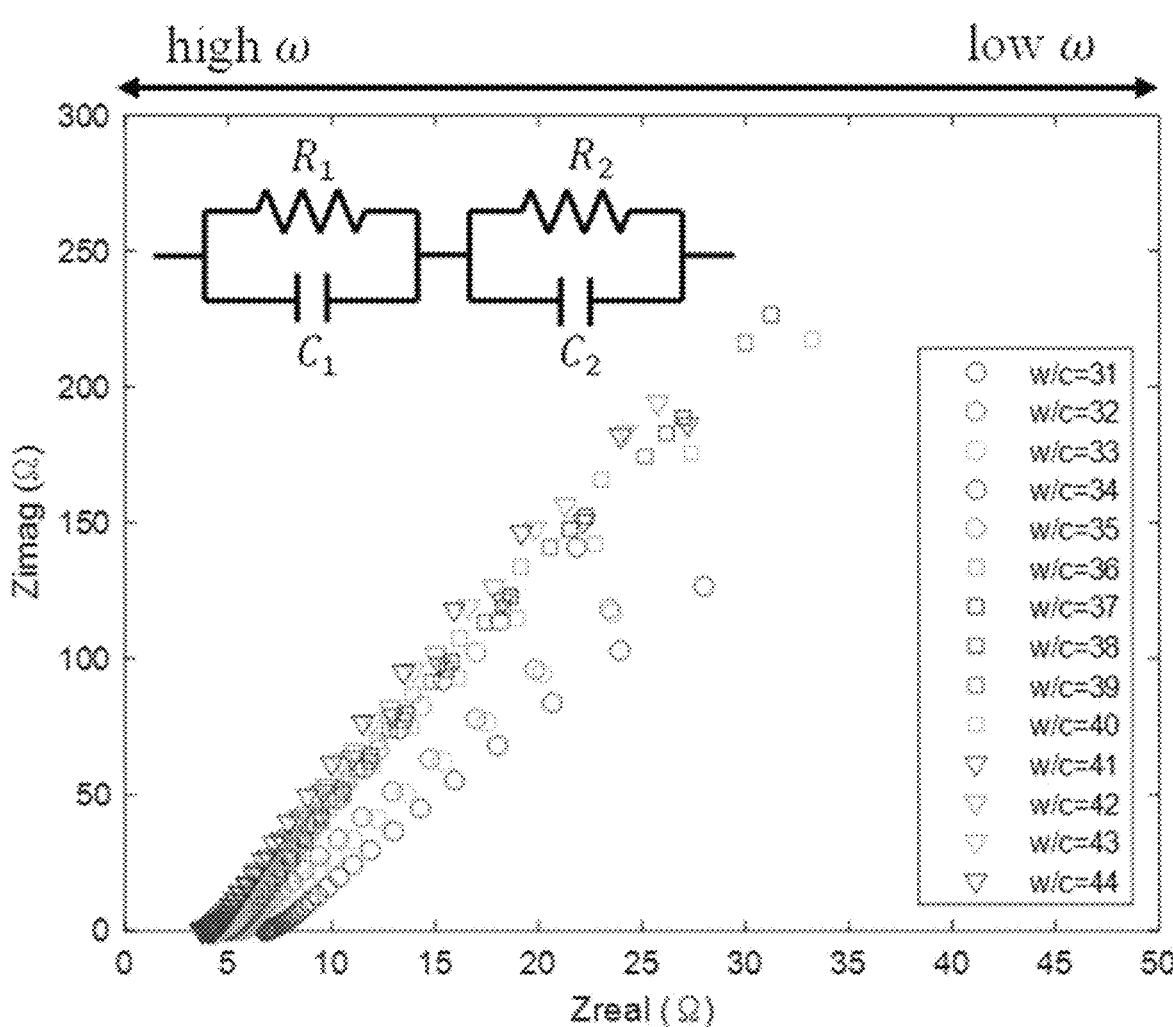
FIG. 3 is a graph of the results of the Nyquist plot according to the EIS test of the cement paste of the present invention.

When such a theoretical model is reconstructed into an equivalent circuit, the circuit passing through the micropores is replaced with a resistance element and the circuit passing through the cement paste is replaced with a capacitor element to have the equivalent circuit shown in FIG. 3. From the viewpoint of the derived impedance (Z), the correlation between the experimental equivalent circuit and the theoretical equivalent circuit can be derived as in Equation 1 below.

$$Z = \frac{(R_{cp}C_{cp}R_{ccp})j\omega + R_{ccp}}{C_{mat}R_{ccp}R_{cp}C_{dp}(j\omega)^2 + (R_{cp}C_{dp} + C_{dp}R_{ccp} + C_{mat}R_{ccp})j\omega + 1} = \qquad \text{[Equation 1]}$$

$$\frac{R_1R_2(C_1 + C_2)j\omega + (R_1 + R_2)}{R_1R_2C_1C_2(j\omega)^2 + (R_1C_1 + R_2C_2)j\omega + 1}$$

$j=\sqrt{-1}$ in Equation 1, $\omega$ has a value of $2\pi f$ as angular frequency and the unit is radian. In addition, $R_1$, $R_2$, $C_1$, $C_2$ in the experimental equivalent circuit are parameters of a theoretical equivalent circuit having a physical meaning of microstructure and can be substituted as Equations 2 to 5.

$$R_{CP} = (R_1 + R_2)\frac{R_1}{R_2}$$ [Equation 2]

$$R_{CCP} = R_1 + R_1$$ [Equation 3]

$$C_{DP} = (C_1 + C_2)\left[\frac{R_2}{(R_1 + R_2)}\right]^2$$ [Equation 4]

$$C_{mat} = \frac{C_1 C_2}{(C_1 + C_2)}$$ [Equation 5]

In the present invention, a correlation between the following normalized variables ($R_{CP}$, $R_{CCP}$, $C_{DP}$, $C_{mat}$) and the cement-based material water-cement ratio is derived through a theoretical equivalent circuit.

The circuit normalization unit 150 normalizes the equivalent circuit reflecting the concrete microstructure based on the impedance experiment using the theoretical equivalent circuit model.

In the present invention, a total of 140 pieces of data were secured to investigate the impedance change according to the water-cement ratio of cement paste using machine learning. The water-cement ratio, a response variable to be known as the result of machine learning, was designed to form a 14-step continuous function from 31% to 44% by the difference of 1%. In order to collect repeatable data for each single water-cement ratio specimen, the specimen was manufactured by repeating 10 times, and impedance spectroscopy was applied.

The specimen is cement paste contained in a cylindrical plastic container with a diameter of 7 cm and a height of 8 cm, and has a constant volume of 300 ml. After putting the measured cement in a container, water was added, mixed evenly for 5 minutes, and compacted 30 times with a 150 mm compaction rod. The detailed mixing information of the specimen is shown in Table 1 below.

TABLE 1

| Mixture | W/C (%) | Unit weight (kg/m³) Cement | Water | Volume (ml) | Number of specimens per mixing ratio (pieces) |
|---|---|---|---|---|---|
| C31 | 31 | 465 | 1499 | 300 | 10 |
| C32 | 32 | 473 | 1477 | 300 | 10 |
| C33 | 33 | 480 | 1455 | 300 | 10 |
| C34 | 34 | 488 | 1434 | 300 | 10 |
| C35 | 35 | 495 | 1414 | 300 | 10 |
| C36 | 36 | 502 | 1394 | 300 | 10 |
| C37 | 37 | 509 | 1375 | 300 | 10 |
| C38 | 38 | 516 | 1357 | 300 | 10 |
| C39 | 39 | 522 | 1338 | 300 | 10 |
| C40 | 40 | 528 | 1321 | 300 | 10 |
| C41 | 41 | 534 | 1304 | 300 | 10 |
| C42 | 42 | 540 | 1287 | 300 | 10 |
| C43 | 43 | 546 | 1270 | 300 | 10 |
| C44 | 44 | 552 | 1254 | 300 | 10 |

The equipment applied to the impedance spectroscopy is Gamry's PCI4/300, and its performance is summarized in Table 2. The impedance measurement equipment applies AC voltage and measures it. That is, it has the advantage of being able to derive the result regardless of the skill level of the experimenter through the predetermined experiment container.

TABLE 2

| | |
|---|---|
| Applied E Range | ±11 V |
| Accuracy | ±2 mV ±0.3% of setting |
| DC Bias | ±8 V |
| Scan Ranges | ±6.4 V, ±1.6 V, ±0.4 V |
| Noise and Ripple | <20 µV rms (1 Hz~10 kHz) |

As an example, the three-electrode method was applied as an experimental method, and a graphite rod having a surface area of 1 cm² was used as a working electrode (WE) and a counter electrode (CE), and a saturated calomel electrode (SCE) was used as a reference electrode.

Each electrode was sequentially inserted into the cement paste by 4 cm and then connected to the PCI4/300 equipment. In the prior art, in the case of cement paste, since bulk arcs observed at high frequencies are not generated, a frequency range of 0.2 Hz to 100 KHz was set, and it was measured for a total of 5 minutes by applying an AC voltage of 10 mV.

Experimental analysis for impedance spectroscopy is based on analysis of a Nyquist plot drawn based on a set equivalent circuit. The Nyquist plot displays the real and imaginary parts of impedance on each axis so that each parameter value can be visually identified. The Nyquist plots for each water-cement ratio are shown in FIG. 3.

As a result of the experiment, bulk arcs were not generated in the low-frequency section due to the characteristics of the aggregate-free cement paste. This means that the value of $C_1$ is very close to 0 so that the impedance of the circuit with the capacitive element in the first half approaches infinity and the current practically does not flow. Therefore, the value $R_1$ representing the bulk resistance can be immediately identified in the high-frequency section, and it was confirmed that it has an average value of about 50.

Figure 4:
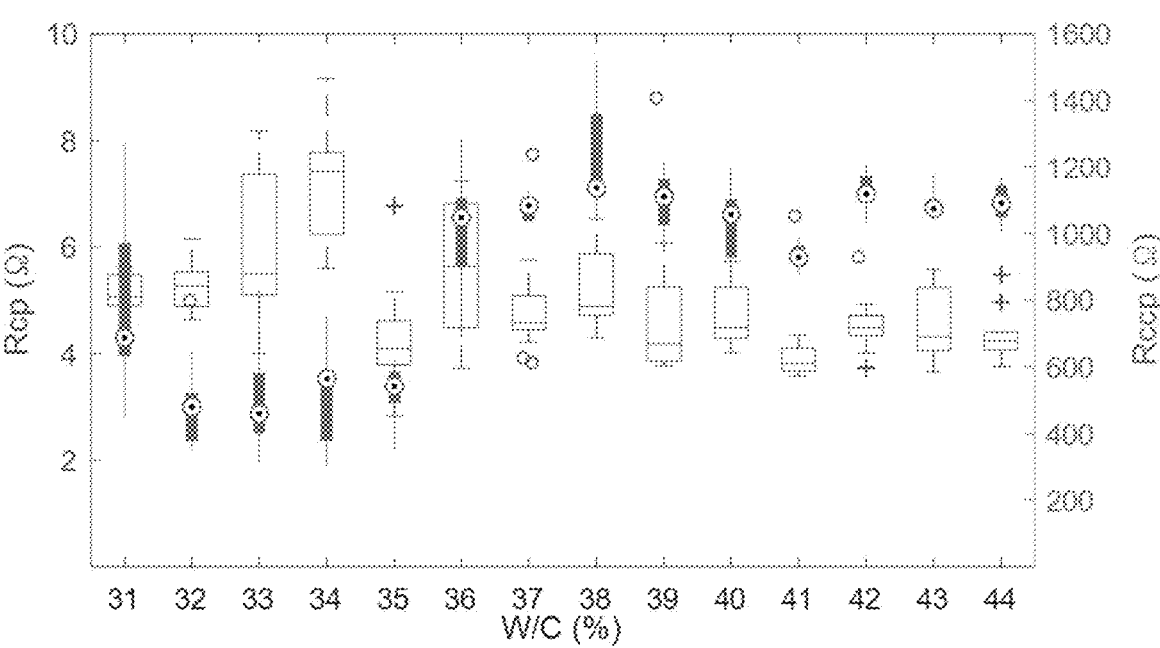
FIG. 4 is a box plot showing the change in resistance, which is a parameter according to the water-cement ratio of the present invention.
Figure 5:
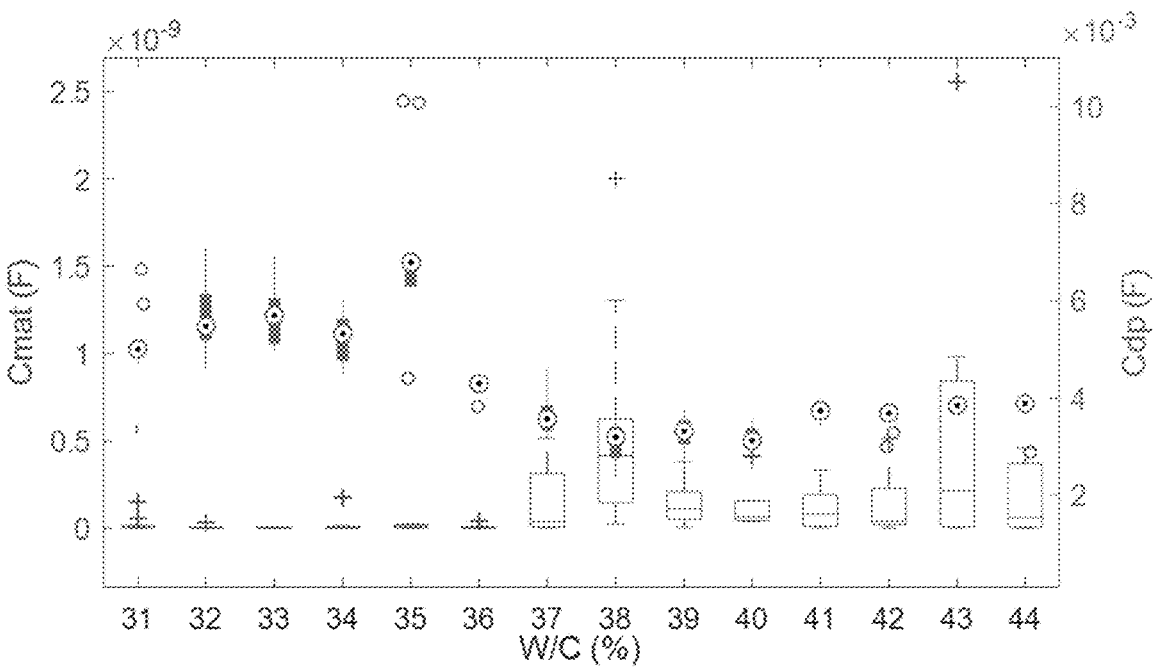
FIG. 5 is a box plot showing the change in capacitance, which is a parameter according to the water-cement ratio of the present invention.

Table 3 is the result of replacing each variable obtained as a result of the experiment with a parameter corresponding to the theoretical equivalent circuit through Equations 2 to 5, and the experimental results according to the water-cement ratio are statistically expressed through the box plot in FIGS. 4 and 5. FIG. 4 shows the change in resistance, which is a parameter according to the water-cement ratio of the present invention, and FIG. 5 shows the change in capacitance, which is a parameter according to the water-cement ratio of the present invention.

TABLE 3

| Mixture | $R_{cp}$ (Ω) Mean | Standard Deviation | $C_{mat}$ (F) Mean | Standard Deviation | $R_{ccp}$ (Ω) Mean | Standard Deviation | $C_{dp}$ (F) Mean | Standard Deviation |
|---------|------|--------------------|------|--------------------|------|--------------------|------|--------------------|
| C31 | 5.08 | 0.39 | $2.45 \times 10^{-11}$ | $4.67 \times 10^{-11}$ | 777.91 | 240.55 | $5.07 \times 10^{-3}$ | $8.51 \times 10^{-4}$ |
| C32 | 5.28 | 0.48 | $3.92 \times 10^{-12}$ | $1.03 \times 10^{-11}$ | 498.65 | 137.81 | $5.68 \times 10^{-3}$ | $7.34 \times 10^{-4}$ |
| C33 | 5.91 | 1.40 | $1.74 \times 10^{-12}$ | $1.73 \times 10^{-12}$ | 501.99 | 155.91 | $5.71 \times 10^{-3}$ | $6.00 \times 10^{-4}$ |
| C34 | 7.18 | 1.13 | $2.05 \times 10^{-11}$ | $5.39 \times 10^{-11}$ | 512.63 | 141.73 | $5.22 \times 10^{-3}$ | $5.25 \times 10^{-4}$ |
| C35 | 4.31 | 1.07 | $8.07 \times 10^{-12}$ | $8.87 \times 10^{-12}$ | 523.50 | 85.39 | $7.09 \times 10^{-3}$ | $1.74 \times 10^{-3}$ |
| C36 | 5.59 | 1.31 | $6.66 \times 10^{-12}$ | $1.20 \times 10^{-11}$ | 1019.75 | 161.48 | $4.27 \times 10^{-3}$ | $1.84 \times 10^{-4}$ |
| C37 | 4.77 | 0.49 | $1.32 \times 10^{-10}$ | $1.87 \times 10^{-10}$ | 1002.61 | 208.97 | $3.71 \times 10^{-3}$ | $5.18 \times 10^{-4}$ |
| C38 | 5.14 | 0.72 | $5.73 \times 10^{-10}$ | $6.33 \times 10^{-10}$ | 1211.92 | 164.82 | $3.10 \times 10^{-3}$ | $3.91 \times 10^{-4}$ |
| C39 | 4.54 | 0.88 | $1.28 \times 10^{-10}$ | $1.18 \times 10^{-10}$ | 1122.39 | 128.40 | $3.24 \times 10^{-3}$ | $4.37 \times 10^{-4}$ |
| C40 | 4.69 | 0.55 | $1.13 \times 10^{-10}$ | $1.15 \times 10^{-10}$ | 1038.36 | 98.55 | $3.14 \times 10^{-3}$ | $3.15 \times 10^{-4}$ |
| C41 | 3.88 | 0.25 | $1.17 \times 10^{-10}$ | $1.18 \times 10^{-10}$ | 943.62 | 50.76 | $3.70 \times 10^{-3}$ | $1.80 \times 10^{-4}$ |
| C42 | 4.45 | 0.36 | $1.30 \times 10^{-10}$ | $1.67 \times 10^{-10}$ | 1113.98 | 81.96 | $3.61 \times 10^{-3}$ | $2.67 \times 10^{-4}$ |
| C43 | 4.52 | 0.69 | $5.39 \times 10^{-10}$ | $7.98 \times 10^{-10}$ | 1084.70 | 43.54 | $3.83 \times 10^{-3}$ | $1.39 \times 10^{-4}$ |
| C44 | 4.35 | 0.53 | $1.55 \times 10^{-10}$ | $1.85 \times 10^{-10}$ | 1094.53 | 56.58 | $3.78 \times 10^{-3}$ | $3.27 \times 10^{-4}$ |
| C45 | 4.32 | 1.13 | $5.98 \times 10^{-12}$ | $7.20 \times 10^{-12}$ | 539.66 | 84.59 | $6.42 \times 10^{-3}$ | $6.78 \times 10^{-4}$ |

The box plot can visually show the maximum, minimum, and median values, and statistical outliers of the parameters derived by repeating 10 times for each water-cement ratio. In the case of statistical outliers, 25% to 75% of data was defined as a box, and data outside 1.5 times the length of the box, that is, data outside the whiskers, were calculated as outliers.

As a result of statistical analysis, since many statistical outliers were not observed, it shows a significant value in terms of the repeatability of the experiment. However, the tendency of each parameter for the water-cement ratio is not easily observed. This is generally the same result as the previous study on cement paste.

The predictive model unit 170 generates a predictive model for estimating the water-cement ratio from parameter values of the equivalent circuit through machine learning.

A predictive model was derived through machine learning to derive a correlation between the parameters obtained through the impedance spectroscopy experiment and the water-cement ratio. The total data for machine learning is a total of 140 sets by repeating the water-cement ratio of 14 steps 10 times each, and one data set comprises normalized parameters ($R_{CP}$, $R_{CCP}$, $C_{DP}$, $C_{mat}$) and water-cement ratio. In this case, $R_{CP}$, $R_{CCP}$, $C_{DP}$, $C_{mat}$ are the predictive variables X to be used for prediction, and the water-cement ratio becomes the predictive response variable Y.

Among the entire data set, training data, and validation data were randomly divided at a ratio of 7:3 within one water-cement ratio. That is, the training data is again divided into a predictive variable (Xtrain) and a response variable (Ytrain), and the response variable (Ypred) estimated by inputting a new predictive variable (Xexp) that is validation data, is compared with the actual response variable (Yexp). The process of dividing into training data and validation data was repeated 10 times to minimize over-fitting and under-fitting problems that may occur in estimating response variables.

In the present invention, three different machine-learning methods were applied. The used methods include Gaussian Process Regression (GPR), Support Vector Regression (SVR), and Decision Tree.

GPR is a technique for interpreting measured data from a stochastic point of view of a Gaussian distribution rather than viewing it as one fixed observation data and is based on the Bayesian law. That is, a probabilistic predictive model is generated based on the measured training data, and in this process, the covariance function (k) is used as a basis. The covariance function applied to the present invention is a basic Squared Exponential (SE) function, and is composed of Equation 6 after optimizing the noise standard deviation (σ).

$$k(x_i, x_j \mid \theta) = \sigma_f^2 \exp\left[-\frac{1}{2} \frac{(x_i - x_j)^T (x_i - x_j)}{\sigma_l^2}\right] \qquad \text{[Equation 6]}$$

Here, the covariance function can be described as a hyperparameter θ ($\sigma_f$, $\sigma_l$, . . . ) function, and expressed as k($x_i$, $x_j$|θ). It consists of predictive variable data $x_i$, $x_j$. In addition, i denotes one point and j denotes one observation point. $\sigma_f$ means the signal standard deviation, and σ means a specific length scale. SVR is a regression technique used when the input variable of the support vector machine (SVM) is continuous rather than categorical, and a similar covariance function can be selected and compared with the GPR model. However, there is a difference in that the algorithm is performed based on specific data (support vector), whereas GPR uses all input data points.

A decision tree generates a predictive model based on a decision tree for regression purposes, not based on a regression function like other models. A decision tree means a classifier that reaches the last leaf node by dividing the entire data along the decision node. The predicted value is obtained by calculating the mean value of the data values belonging to the leaf nodes.

Machine learning applied to the present invention was performed based on a commercial program, Matlab, and the used codes are attached in Table 4. The time taken to perform each machine learning model once on one data set was about 123, 130, and 100 seconds depending on GPR (SE), SVR, and decision tree, respectively.

TABLE 4

```
%%%% Divide the data %%%%
gprMdl = { }; Y_eval = { }; legend_string = { }; n_fit
= 1; Xtrain=[ ];, Ytrain=[ ];, Xtest=[ ];, Ytest=[ ];        %Expectation
for i=1:15;                                                 [Y_eval(1,n_fit], ~] = predict(gprMdl(1,n_fit},
```

11 12

TABLE 4-continued

```
xx=DT{i,2}; yy=DT{i,1};                        Xtest);
cv = cvpartition (size (xx,1),'Holdout',0.3);   %Calculate the MSE
idx = cv.test;                                  L{1,n_fit} = loss(gprMdl(1,n_fit), Xtest, Ytest);
Xtrain = vertcat(Xtrain,xx(~idx,:));
Xtest = vertcat(Xtest,xx(idx,:));
Ytrain = vertcat(Ytrain,yy(~idx,:));            legend_string{1,n_fit}
Ytest = vertcat(Ytest,yy(idx,:));               %% Method #3: Fit SVR (Gaussian kernel)
end                                             %Training
%%%% Create and train the model%%%%             gprMdl{1,n_fit]                            =
%% Method #1: Fit GPR (SE)                      fitrsvm(Xtrain,Ytrain,'KernelFunction','gaussian',
%Training                                       'KernelScale','auto','Standardize',1);
gprMdl(1,n_fit}                            =    %Expectation
fitrgp(Xtrain,Ytrain,'OptimizeHyperparameters',{'K  Y_eval{1,n_fit}]] = predict(gprMdl{1,n_fit}, Xtest);
e r n e l S c a l e ' , ' S i g m a ' } ,       %Calculate the MSE
'Standardize',1,'HyperparameterOptimizationOptions
',struct('MaxObjectiveEvaluations',100,'Verbose',1  L{1,n_fit} = loss(gprMdl{1,n_fit}, Xtest, Ytest) ;
,'ShowPlots',false));                           legend_string{1,n_fit} = 'SVR';
%Expectation                                    n_fit = n_fit + 1;
[Y_eval{1,n_fit}, ~] = predict (gprMdl{1,n_fit},  %% Method #4: Fit Decision Tree(Bayesian
Xtest);                                         Optimization)
                                                %Training
                                                gprMdl{1,n_fit}]                           =
%Calculate the MSE                              fitrtree(Xtrain,Ytrain,'OptimizeHyperparameters','
L{1,n_fit} = loss(gprMdl(1, n_fit}, Xtest, Ytest);  a   l   l   '   ,
legend_string{1,n_fit}] = 'GPR (SE)';           'HyperparameterOptimizationOptions',struct{'MaxObj
n_fit =n_fit + 1;                               ectiveEvaluations',100,'Verbose',1,'ShowPlots', fal
                                                se));
%% Method #2: Fit GPR (Adaptive) based on Bayesian  %Expectation
Optimization                                    Y_eval(1,n_fit) = predict(gprMdl{1,n_fit), Xtest) ;
%Training
gprMdl(1,n_fit}                            =    %Calculate the MSE
fitrgp(Xtrain,Ytrain,'OptimizeHyperparameters',{'K  L(1,n_fit} = loss(gprMdl(1,n_fit}, Xtest, Ytest);
ernel Function','KernelScale','Sigma'},
Standardize',1,'HyperparameterOptimizationOptions'  legend_string{1,n_fit} = 'Decision Tree';
,struct ('MaxObjectiveEvaluations',100,'Verbose',1,  n_fit = n_fit + 1;
'ShowPlots',false));
```

Figure 6:
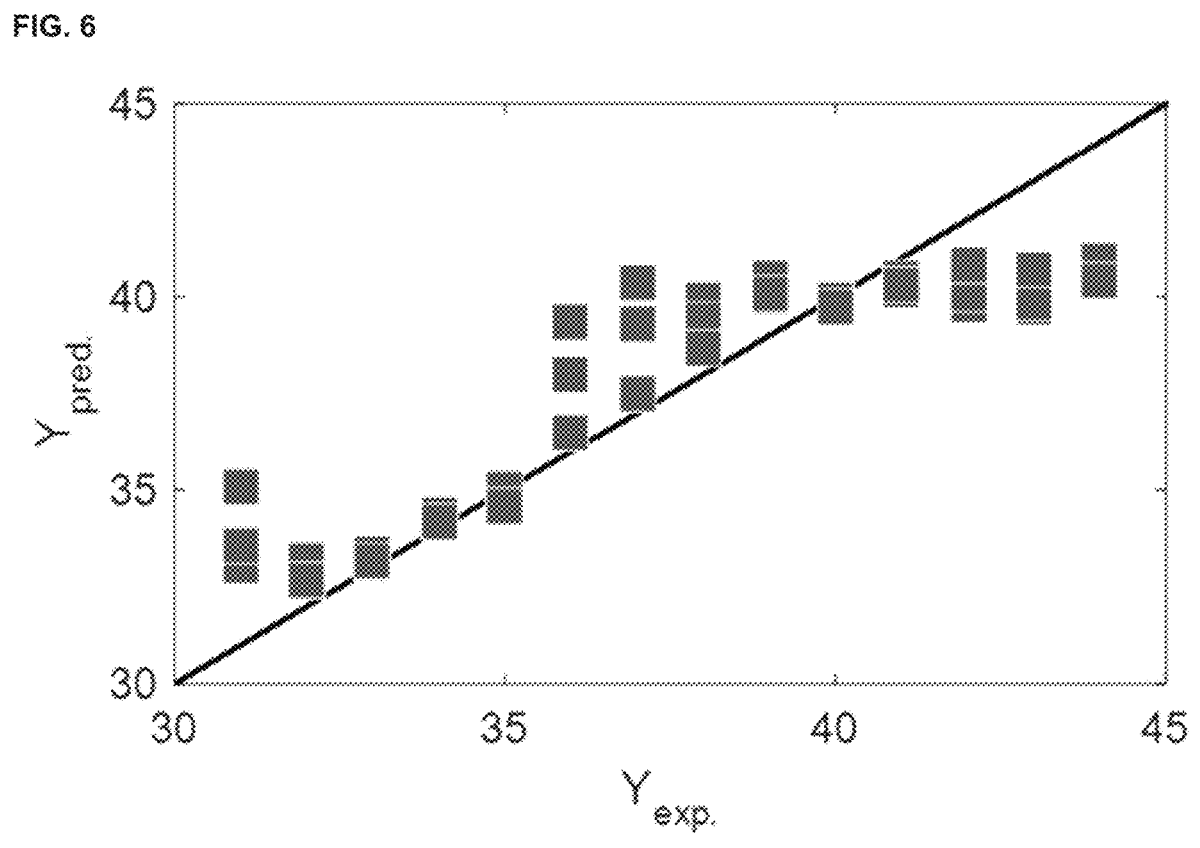
Figure 7:
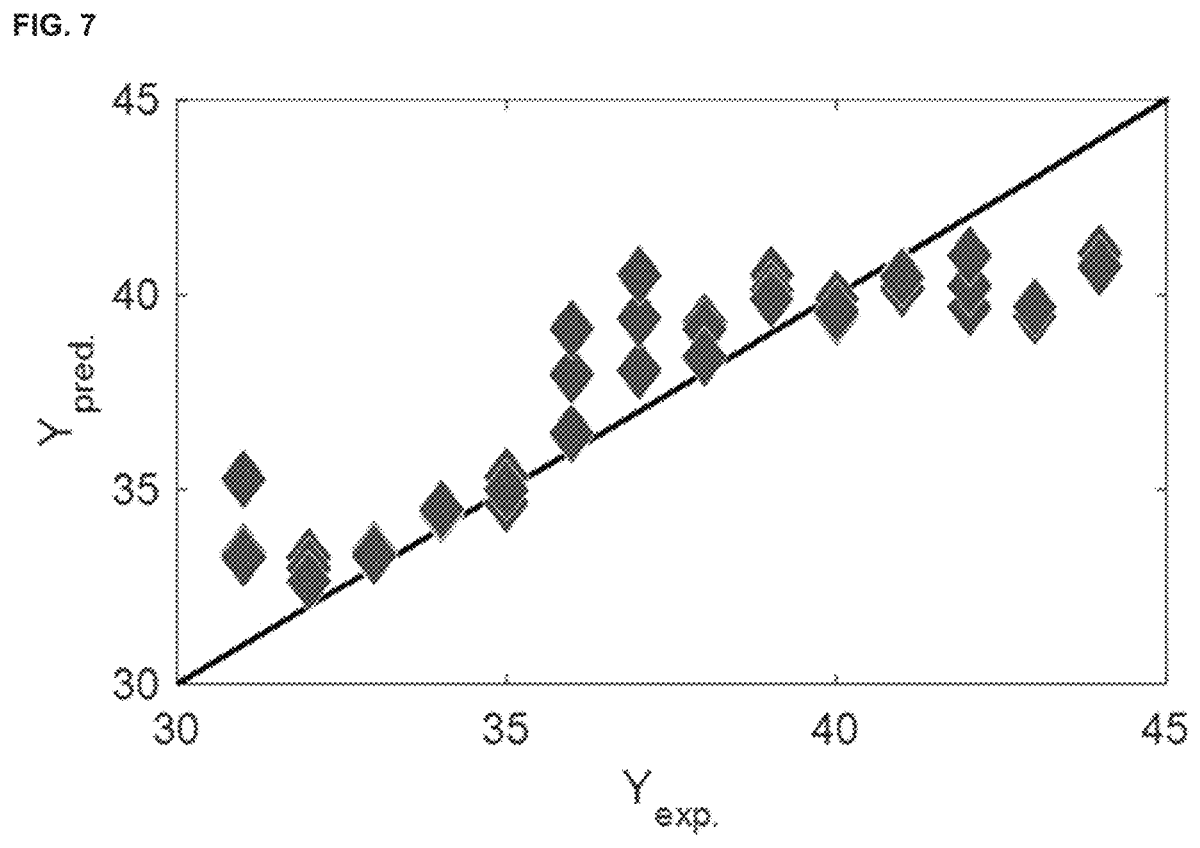
Figure 8:
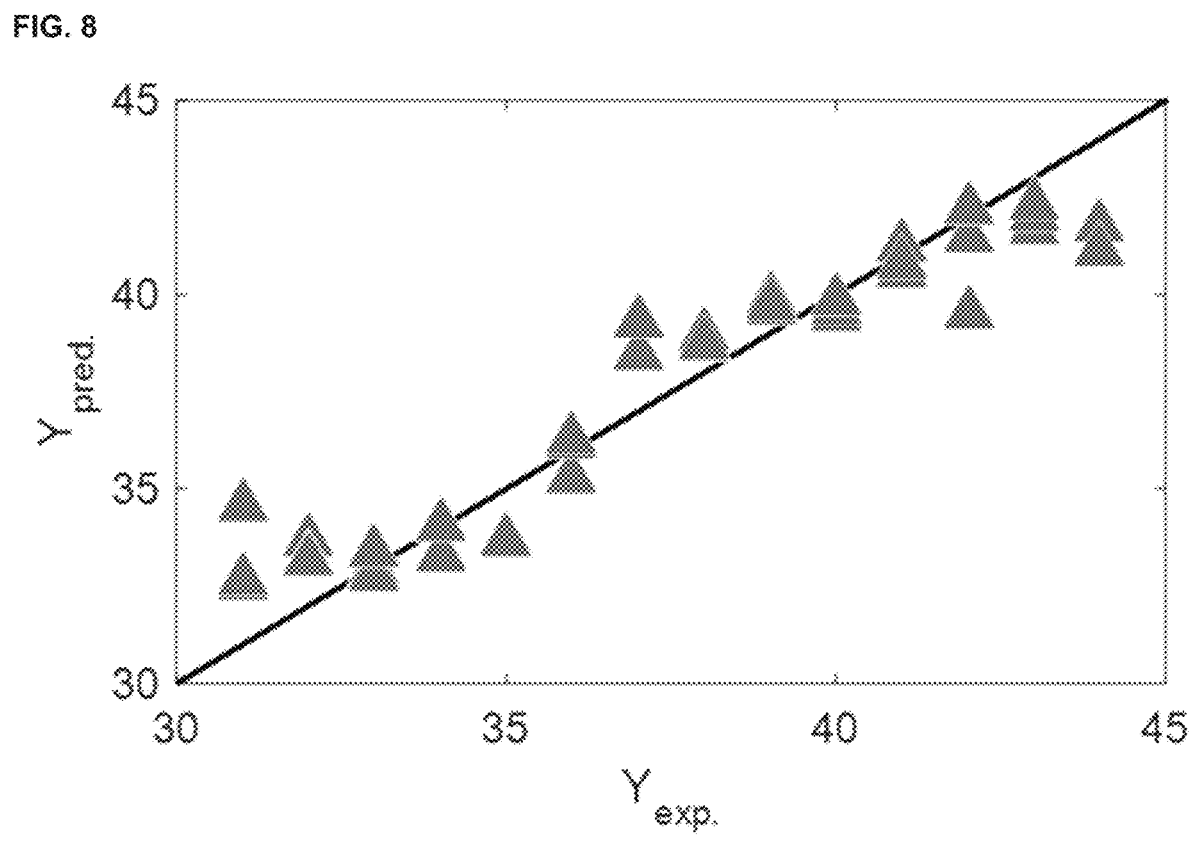

FIGS. 6 to 8 show the results of applying each machine learning model as a graph. FIGS. 6-8 are graphs of water-cement ratio prediction results according to a machine-learning model using a square exponential function GPR, a machine-learning model using SVR, and a machine-learning model using a decision tree, respectively.

The X-axis of the graph is the actual water-cement ratio applied to the experiment, which is the response variable (Yexp), and the Y-axis is the response variable (Ypred) estimated by inputting the new predictive variable (Xexp), which is validation data. The diagonal of the graph is an absolute line where the predictive value and the actual value coincide, and the closer the data is to the line, the higher the accuracy of the predictive model.

Table 5 is the calculated value for the regression error that occurs when new data is put into the predictive model.

TABLE 5

|  | GPR (SE) | SVR | Decision Tree |
|---|---|---|---|
| 1 | 11.55 | 10.50 | 9.70 |
| 2 | 11.16 | 11.70 | 10.40 |
| 3 | 12.30 | 12.02 | 11.43 |
| 4 | 10.26 | 10.52 | 9.62 |
| 5 | 11.33 | 8.98 | 8.34 |
| 6 | 12.87 | 10.97 | 10.39 |
| 7 | 10.86 | 9.51 | 11.89 |
| 8 | 11.10 | 10.73 | 10.58 |
| 9 | 12.26 | 12.17 | 16.03 |
| 10 | 16.68 | 12.10 | 12.00 |
| MAE | 2.54 | 2.11 | 2.10 |
| MSE | 10.39 | 9.06 | 8.59 |
| RMSE | 3.22 | 3.01 | 2.93 |

The regression error was calculated as the mean absolute error (MAE), mean squared error (MSE), and root mean squared error (RMSE) of Equations 7 to 9 below, respectively.

$$MAE = \frac{1}{n}\sum_{i=1}^{n}|Yi - \hat{Y}i|$$ [Equation 7]

$$MSE = \frac{1}{n}\sum_{i=1}^{n}(Yi - \hat{Y}i)^2$$ [Equation 8]

$$RMSE = \sqrt{\frac{1}{n}\sum_{i=1}^{n}(Yi - \hat{Y}i)^2}$$ [Equation 9]

Here, $Y_i$ is the actual response variable, $\hat{Y}_i$ is the ith estimated response variable, and n is the total data size. In all of MAE, MSE, and RMSE, the smaller the value, the better the prediction performance. The characteristics of each regression error are as follows. In the case of MAE, it is a simple error between the predictive value and the actual value, and it shows the result intuitively. MSE is the average of the squared differences between the actual value and the predictive value, and is most commonly used, but is sensitive to outliers. RMSE is the conversion of MSE back to units similar to actual values. Since the data is randomly partitioned, it can be seen that the best-performing model is different for each iteration of machine learning. In order to supplement reliability, the estimated response variable model (Ypred), which was averaged after running 10 times, was finally used.

As a result of applying the final estimated response variable model, the predictive performance of the Decision Tree, which showed the lowest all regression errors, was the best. Based on the best predictive model, it can be identified that the water-cement ratio of cement paste is possible within the error range of about MAE 2.10, MSE 8.59, and RMSE 2.93 through the impedance spectroscopy. However, this result was verified for cement paste with a water-cement ratio of 31 to 44% and can be extended to various case-by-case material mixings.

Figure 9:
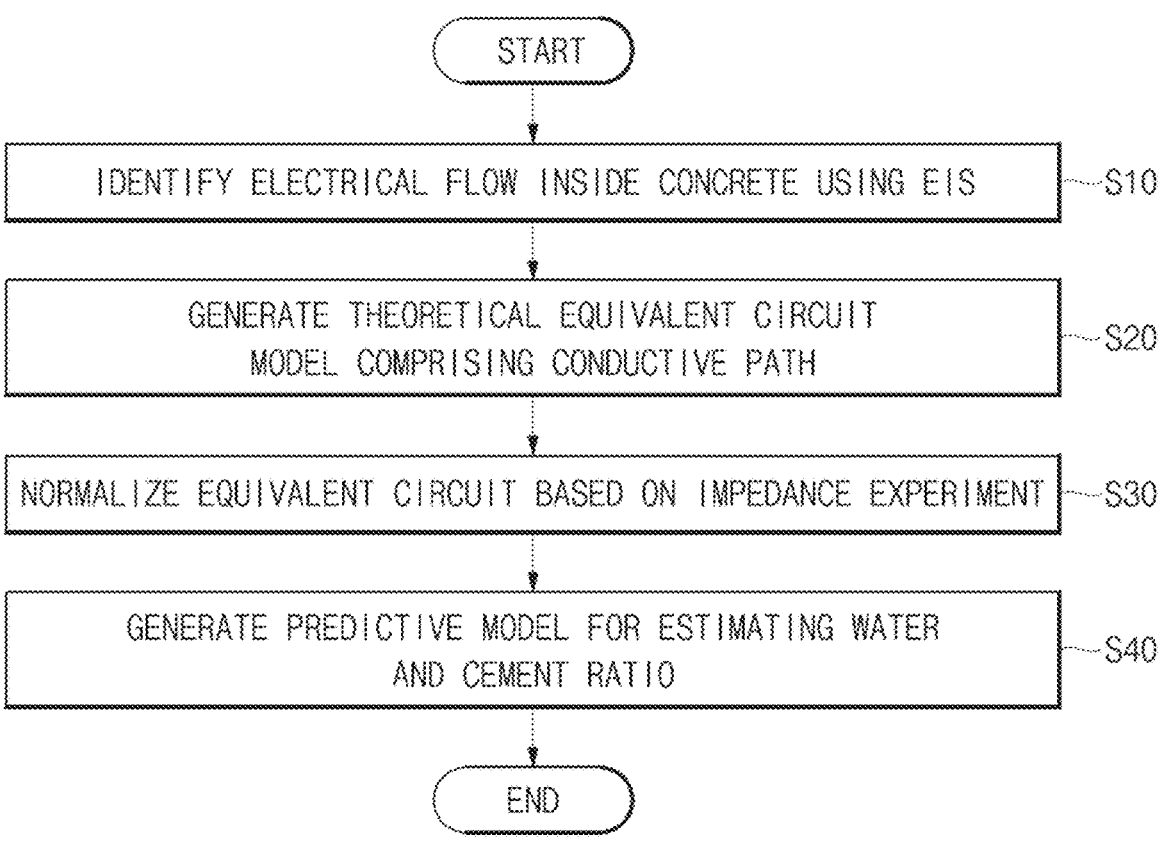
FIG. 9 is a flowchart of an impedance spectroscopy analytical method for concrete using machine learning according to an embodiment of the present invention.

FIG. 9 is a flowchart of an impedance spectroscopy analytical method for concrete using machine learning according to an embodiment of the present invention.

The impedance spectroscopy analytical method for concrete using machine learning according to the present embodiment may be performed in substantially the same configuration as the apparatus 10 of FIG. 1. Accordingly, components identical to those of the apparatus 10 of FIG. 1 are given the same reference numerals, and repeated descriptions are omitted.

In addition, the impedance spectroscopy analytical method for concrete using machine learning according to the present embodiment may be executed by software (application) for performing an impedance spectroscopy analysis for concrete using machine learning.

Referring to FIG. 9, the impedance spectroscopy analytical method for concrete using machine learning according to the present embodiment identifies the electrical flow through the moisture and conductive ions present in the concrete using a node for measuring electricity based on electrochemical impedance spectroscopy (EIS) (step S10).

In this case, a three-electrode method using a working electrode (WE), a counter electrode (CE), and a reference electrode can be applied.

A theoretical equivalent circuit model comprising a conductive path reflecting the electrical flow is generated (step S20).

An equivalent circuit reflecting the concrete microstructure is normalized based on the impedance experiment using the theoretical equivalent circuit model (step S30). The microstructure of the concrete is a cement matrix and internal voids.

A predictive model for estimating the water-cement ratio is generated from the parameter values of the equivalent circuit through machine learning (step S40). The parameter values may be the resistance and capacitance of the equivalent circuit.

The machine learning may use the square exponential function Gaussian Process Regression (GPR), Support Vector Regression (SVR), and a decision tree.

In the present invention, an algorithm for estimating the water-cement ratio of unhardened cement-based materials was established, and the model with the best predictive performance when tested on cement paste predicted a water-cement ratio within an error of about MAE 2.10, MSE 8.59, and RMSE 2.93.

By installing electrodes on unhardened cement-based materials, it is possible to immediately respond to changing conditions in the field through electrical measurements, and accordingly derive mixing information such as the water-cement ratio.

The development of simple, automated and highly reliable field test methods by systematizing quality control tasks, which have been performed based on existing manpower, based on machine learning can be expected.

Such an impedance spectroscopy analytical method for concrete using machine learning may be implemented as an application or implemented in the form of program instructions that can be executed through various computer components and recorded on a computer-readable recording medium. The computer-readable recording medium may include program instructions, data files, data structures, etc. alone or in combination.

Program instructions recorded on the computer-readable recording medium may be those specially designed and configured for the present invention, or those known and usable to those skilled in the art of computer software.

Examples of a computer-readable recording medium include magnetic media such as hard disks, floppy disks, and magnetic tapes, optical recording media such as CD-ROMs and DVDs, and magneto-optical media such as floptical disks, and hardware devices specially configured to store and execute program instructions, such as ROM, RAM, flash memory, and the like.

Examples of program instructions include high-level language codes that can be executed by a computer using an interpreter or the like as well as machine language codes such as those produced by a compiler. The hardware device may be configured to act as one or more software modules to perform processing according to the present invention and vice versa.

Although the above has been described with reference to embodiments, it can be understood that those skilled in the art can variously modify and change the present invention without departing from the spirit and scope of the present invention described in the claims below.

The present invention can inversely estimate material mixture and predict durability and can be used as basic data for developing reliable quality control techniques for unhardened concrete at construction sites.

In addition, the present invention can contribute to the development of a simple, automated and highly reliable field test method by systematizing the quality control work, which has been performed based on existing manpower, based on machine learning.

REFERENCE NUMERAL

10: impedance spectroscopy analytical apparatus for concrete using machine
learning
110: EIS unit
130: equivalent circuit unit
150: circuit normalization unit
170: predictive model unit
The invention claimed is:

1. An impedance spectroscopy analytical method for concrete using machine learning comprising:
   identifying electrical flow through moisture and a conductive ion present in concrete using a node that measures electricity based on Electrochemical Impedance Spectroscopy (EIS);
   generating a theoretical equivalent circuit model comprising a conductive path reflecting the electrical flow;
   normalizing an equivalent circuit reflecting a concrete microstructure based on an impedance experiment using the theoretical equivalent circuit model; and
   generating a predictive model for estimating a water and cement ratio from a parameter value of the equivalent circuit through machine learning,
   wherein identifying the electrical flow applies a three-electrode method using a working electrode (WE), a counter electrode (CE), and a reference electrode.
2. The method of claim 1, wherein the concrete microstructure includes a cement matrix and an internal void.
3. The method of claim 1, wherein the machine learning uses at least one model of square exponential function Gaussian Process Regression (GPR), Support Vector Regression (SVR), and Decision Tree.

4. The method of claim 1, wherein the parameter value includes resistance and capacitance of the equivalent circuit.

5. A non-transitory computer-readable storage medium, on which a computer program for performing the impedance spectroscopy analytical method for concrete using machine learning according to claim 1 is recorded.

6. An impedance spectroscopy analytical apparatus for concrete using machine learning comprising:

an Electrochemical Impedance Spectroscopy (EIS) unit for identifying electrical flow through moisture and a conductive ion present in concrete using a node that measures electricity based on EIS;

an equivalent circuit unit for generating a theoretical equivalent circuit model comprising a conductive path reflecting the electrical flow;

a circuit normalization unit for normalizing an equivalent circuit reflecting a concrete microstructure based on an impedance experiment using the theoretical equivalent circuit model; and a predictive model unit for generating a predictive model for estimating a water and cement ratio from a parameter value of the equivalent circuit through machine learning, wherein the EIS unit applies a three-electrode method using a working electrode (WE), a counter electrode (CE), and a reference electrode.

7. The apparatus of claim 6, wherein the concrete microstructure includes a cement matrix and an internal void.

8. The apparatus of claim 6, wherein the machine learning uses at least one model of square exponential function Gaussian Process Regression (GPR), Support Vector Regression (SVR), and Decision Tree.

9. The apparatus of claim 6, wherein the parameter value includes resistance and capacitance of the equivalent circuit.

* * * * *